US006695770B1

(12) United States Patent
Choy et al.

(10) Patent No.: US 6,695,770 B1
(45) Date of Patent: Feb. 24, 2004

(54) SIMULATED HUMAN INTERACTION SYSTEMS

(75) Inventors: Dominic Kin Leung Choy, 28 Cowdroy Avenue, Cammeray, New South Wales 2062 (AU); Stuart Davies, Southport (AU); Eddie Lim, Willoughby (AU)

(73) Assignee: Dominic Kin Leung Choy, New South Wales (AU)

( * ) Notice: Subject to any disclaimer, the term of this patent is extended or adjusted under 35 U.S.C. 154(b) by 0 days.

(21) Appl. No.: 09/937,811

(22) PCT Filed: Apr. 3, 2000

(86) PCT No.: PCT/AU00/00279

§ 371 (c)(1), (2), (4) Date: Feb. 19, 2002

(87) PCT Pub. No.: WO00/59581

PCT Pub. Date: Oct. 12, 2000

(30) Foreign Application Priority Data

Apr. 1, 1999 (AU) ............................................. PQ2641

(51) Int. Cl.[7] ................................................ A61F 5/00
(52) U.S. Cl. ................................................... 600/38
(58) Field of Search ....................... 600/38; 128/897–98

(56) References Cited

U.S. PATENT DOCUMENTS

| | | | | |
|---|---|---|---|---|
| 5,490,784 A | * | 2/1996 | Carmein | 434/55 |
| 6,368,268 B1 | * | 4/2002 | Sandvick et al. | 600/38 |

* cited by examiner

*Primary Examiner*—John P. Lacyk
(74) *Attorney, Agent, or Firm*—Olson & Hierl, Ltd.

(57) ABSTRACT

An apparatus for providing a virtual reality sexual experience. The apparatus including audio reproduction means, visual reproduction means and tactile means for sexual stimulation. The apparatus further comprising a control system to correlate the audio means, visual means and tactile means to relate to one another to simulate a sexual experience. The apparatus being adapted for connection to a computer based drive system to provide a scenario for audio and visual outputs which is selected from a database and advances in a manner corresponding to user movements and engagement with the tactile system.

16 Claims, 3 Drawing Sheets

SIMULATED HUMAN INTERACTION SYSTEMS

FIELD OF THE INVENTION

The present invention relates to simulated human interactive systems and more particularly is concerned with a system using virtual reality to simulate an environment and provide a sexual experience.

BACKGROUND OF THE INVENTION

Virtual reality systems can provide a range of simulated environments, the user typically having a headset linked to a computer system and providing visual images and audio input to the user. Such virtual reality systems have been applied to a number of applications including games and can also be used in a training environment.

It is well recognised that audio and/or visual signals particularly containing erotic materials can be a most powerful sexual stimulus and similarly touch is also a powerful stimulus.

However, there is generally a synergy between the three elements of touch, audio and visual stimulation yet hitherto the best experience offered is erotic videos which can assist viewers in gaining intense sexual experience as a result of mental stimulation probably based on fantasising on the basis that the viewer is participating with the person or persons depicted in the video. The sexual experience, however, is limited to participation with a sexual partner also viewing the material or by the use of sexual toys or masturbation.

SUMMARY OF THE INVENTION

The present invention is based on the concept of providing a new combination of features offering a substantial advance in the potential to heighten human stimulation in a virtual environment to achieve more intense sexual satisfaction. In one aspect the present invention consists in an apparatus for providing a virtual reality sexual experience, the apparatus including audio reproduction means, visual reproduction means and tactile means for sexual stimulation, the apparatus further comprising a control system to correlate the audio means, visual means and tactile means to relate to one another to simulate a sexual experience, the apparatus being adapted for connection to a computer based drive system to provide a scenario for audio and visual outputs which is selected from a database and advances in a manner corresponding to user movements and engagement with the tactile system.

BRIEF DESCRIPTION OF THE DRAWINGS

In the FIGURES.

Figure 1:
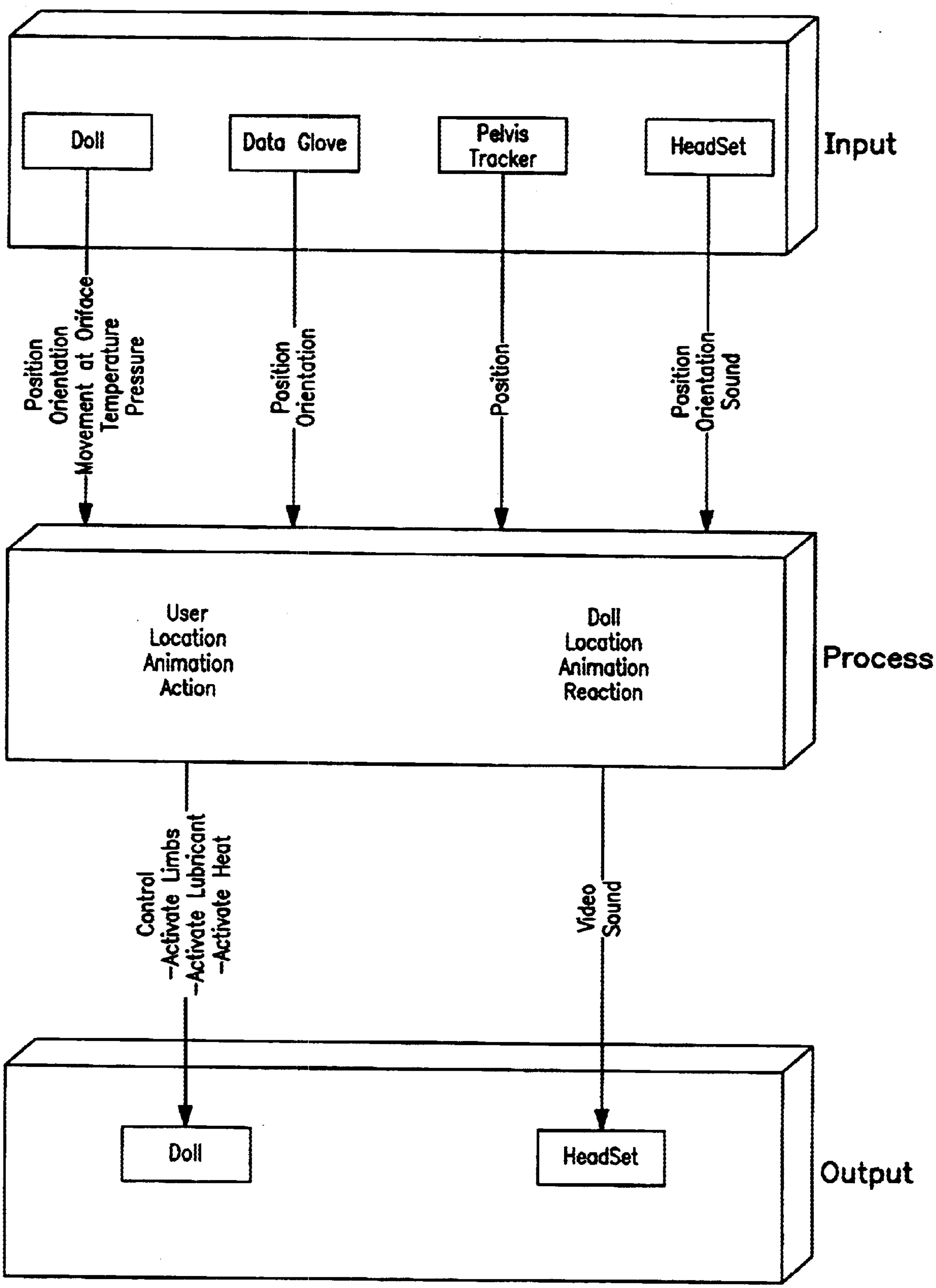
FIG. 1 is a data flow diagram illustrating signal processing during the practice of the invention.

Preferably the apparatus is used with a head mounted display system and a movement and position sensing device applied to a critical part or parts of the body of the user. For example, the sensing device could be in the form of a digital glove type device which fits over the hand or the back of the hand of the user and from an initial position tracks movement and causes visual images and corresponding sounds to be selected from the database in a corresponding manner.

The system (hardware and software) will allow a user to enter a virtual world and have a sexual experience with a virtual human, or indeed another real human who is also linked up to the same world.

In the case of a single user version, the user will be able to select with whom they wish to interact with (a film star for instance). These virtual actors can be represented as highly detailed texture mapped polygonal models and the physical contact itself is simulated by use of a haptic device, in this case a life-sized doll, which is controlled by the software.

Thus, the invention may be implemented with the apparatus including a mannequin or doll or a part thereof fitted with appropriate sensors which are connected to the control system to advance the audio and visual outputs corresponding to user movement or manipulation of the mannequin or doll. In a simplified form the mannequin or doll could be replaced with devices being artificial versions of human body parts used in sexual activities, for example artificial male or female genitalia as well as or replaced by devices for use in simulating oral sexual activities.

Most preferably, however, the invention is applied using a mannequin or doll and preferably sensor are provided to be responsive to touch to various portions of the doll, whereby the control system can cause the visual output to correspond but in addition sensors responsive to movement temperature and pressure and motion can be provided to initiate a physical reaction in the mannequin e.g. discharge of lubrication, generation of heat and vibration or suction effects.

The engineering cost of applying the invention with a full body doll which can provide human-like sexual movements would be an expensive implementation and therefore it is envisaged that a more economical embodiment of the invention would be one in which the doll can engage in limited movements but generally is aimed at being essentially passive. However, sexual organs can be appropriately motor driven. For example, in the case of a male doll, the penis could be motorised to respond to user activity to provide intense stimulation beyond the range of human movement. For example, the penis could be driven not only to reciprocate at selected or varying speeds but also to rotate, vibrate, and to discharge fluid.

The invention can be applied using a suitable modern computer system such as a relatively high specification personal computer with suitable controlling software.

The full system when set us for use will typically comprise a relatively high performance personal computer with controlling software and loaded data from which the user can select from one of a multiplicity of stored sexual scenarios. The user wears a virtual reality headset and a motion tracking device adapted to be applied to the user's body, for example, in the manner of a belt in order to track the user's body motion. In a more sophisticated version there may be a multiplicity of sensors detecting motion of different parts of the body. Furthermore, a data glove or similar device would be applied to at least one hand of the user in order to track motion and to provide signals to the system for controlling advance of the stored visual scenario. The final main component of the system is the mannequin or doll with sexually responsive parts.

In a preferred embodiment control of the system is through the data glove or equivalent device. This is used by user physical movements to e.g. select from menus in the computer system.

Embodiments of the present invention are also able to be used where instead of the mannequin or doll a sexual partner is used and each of the users can have their own headsets and for example, can be provided with images of selected movie stars or the image of any person with whom the user wishes to fantasise.

Preferably the system includes input devices which have six degrees of freedom for orientation and positioning.

At least one, and preferably most of the following features, are provided:

1. User movements must be monitored and his avatar must move appropriately.
2. If the user interacts with the virtual environment (for instance to pick up an object) that object must move appropriately.
3. If the user touches the virtual human, the virtual human must react appropriately. The skin must also deform and move as it would in the real world.
4. The virtual humans facial expressions must be conveyed realistically, and be linked to whatever the user does.
5. Some form of feedback is required so that the user can ‘feel’ whatever he is touching.
6. In terms of a 2-user scenario, a networked system will be required, which is capable of transmitted user movements, etc in real time.
7. The virtual human must be capable of reacting to the user. For instance, if the user touches the virtual human, it should elicit some form of facial or verbal response depending on how the user touches.
8. Sound is an important factor I creating realism. Sound must be positioned within 3D space so that it appears that it is emanating from a particular point within the virtual environment.
9. The virtual human must be able to speak (or make noises) via their mouth. The mouth must be in sync with the noise.
10. Virtual human animation must be realistic and fluid.

For illustrative purposes only examples will now be given of system components.

Virtual Reality Headset

A suitable commercially available headset is envisaged. The headset should have tracking ability with six degrees of freedom, communicate through a radio frequency link, be lightweight, provide stereo audio and crisp images. One example is a Kaiser XL50 headset.

The XL50 is the newest addition to the ProView™ family of head-mounted displays. It features full-color XGA performance for those demanding tasks that require ultra-high resolution stereo imagery.

The ProView™ XL50 incorporates Kaiser Electro-Optics’ (KEO) proprietary technology to achieve unparalleled color performance and high contrast ratio. The expanded color gamut really sets it apart from other display systems.

11. The optical modules are mounted on the same comfort-fit headband system used on all ProView™ HMDs.

| Performance Parameters* (also available as an monocular unit) | | |
|---|---|---|
| DISPLAY | Type LCD<br>Resolution/<br>Eye<br>Brightness | Full color, active matrix TFT, high speed polysilicon LCDs, XGA Resolution (1024 × 768) XGA resolution is 1024 horizontal pixels by 768 vertical lines |

-continued

| Performance Parameters* (also available as an monocular unit) | | |
|---|---|---|
| | Contrast | 2.34 arcmin/color group |
| | | 5–50 fL (adjustable) |
| | | ≧40:1 |
| OPTICAL | Field of View | 50° diagonal, 30° (V) × 40° (H) |
| | Transmission | Non see-through |
| | Optics | Color-corrected, aspheric refractive |
| | Eye Relief | lens - independent optical paths for |
| | | each eye |
| | Exit Pupil | Eyeglasses compatible |
| | Overlap | Non pupil forming |
| | Stereo/Mono | 100% |
| | Color | Yes |
| | Coordinates | Red: u' = 0.5099 v' = 0.5228 |
| | | Green u' = 0.1033 v' = 0.5774 |
| | | Blue u' = 0.1314 v' = 0.2250 |
| MECHAN- | IPD | Independent left/right |
| ICAL | IPD Range | 55–75 mm |
| | HMD Weight | ounces |
| | Headtracker | Accommodates magnetic and inertial |
| | | tracker sensors |
| CONTROL | Video Inputs | One or two XGA 1024 × 768, H & V - |
| UNIT | Horizontal Scan | TTL, Analog 0.7 V P-P, 75 ohms, 60 |
| | Rate | Hz video inputs Autosense for stereo- |
| | | scopic or monoscopic operation |
| | Vertical Scan | Internal and external sync |
| | Rate | 48.363 kHz |
| | Genlocked | 60.004 kHz |
| | Inputs | Independent phased locked loops for |
| | Cable Length | left and right eye |
| | Video Outputs | 20 feet |
| | Controls | 2 XGA video loops to display monitor |
| | Indicators | Audio adjust |
| | (LED) | Power on/off |
| | Connectors | Video in |
| | Power | XGA, 15 pin DA, female, (video in) 2 |
| | | XGA, 15 pin DA, female, (video out for |
| | | monitor) 2 |
| | | BNC barrel connectors, RGB H & V, |
| | | (video in) 2 sets |
| | | RCA connectors, (stereo audio com |
| | | pass through) 2(cables are not provided |
| | | to either video or audio connectors) |
| | | 85–264 VAC, 47–440 Hz, 25 W (power |
| | | cable included) |

Body Motion Tracker

In one embodiment body motion tracking is in the form of a belt which will respond to the motion of the user’s pelvis. Six degrees of freedom for position and. orientation are required and set out below is a technical specification illustrative of a current commercially available motion tracker.

Body Motion Tracker

This will be in the form of a belt which will record the motion of the user's pelvis.

| • Wireless | | |
|---|---|---|
| TECHNICAL | Degrees of Freedom: | 6: (position and orientation) |
| | Telemetry: | 14 receivers per performer plus digital and analog inputs for user devices |
| | Translation range: | ±10' in any direction |
| | Angular range: | All-attitude: ±180° Azimuth & Roll, ±90° Elevation |
| | Accuracy: | |
| | • position | 0.3 inch RMS at 5-ft range, 0.6 inch RMS at 10-ft range |
| | • orientation | 0.5° RMS at 5-ft range, 1.0° RMS at 10-ft range |
| | Resolution: | |
| | • position | 0.03 inch at 5-ft range, 0.10 inch at 10-ft range |
| | • orientation | 0.1° RMS at 5-ft range, 0.2° RMS at 10-ft range |
| | Update rate: | Up to 120 measurements/second |
| | Outputs: | X, Y, Z position and orientation angles, rotation matrix, or quaternions |
| | Interface: | Ethernet, RS-232C |
| | Line-of-sight restrictions: | None |
| | Metallic Distortion: | Minimal, Large metallic objects should be removed from the motion-capture stage |
| PHYSICAL | Peformer-Mounted Components: | |
| | Sensors: | L × W × H 1.0" × 1.0" × 0.8" (attached via wires to electronics unit in fanny pack). Weight 0.6 oz per sensor without cable |
| | Electronics Unit: | L × W × H 6.9" × 5.5" × 2.0" Weight 35 oz |
| | Battery: | L × W × H 5.9" × 1.6" × 1.0" Weight 19 oz Operating time: 2 hrs continuous |
| | Base-Station Components: | |
| | MotionStar Chassis: | L × W × H 18" × 19" × 10" Weight 45 lbs |
| | Remote Receiver Unit: | L × W × H 6.5" × 4.2" × 2.5" Weight 0.7 lbs |
| | Extended Range Controller: | L × W × H 9.5" × 11.5" × 4.8" Weight 6.5 lbs. |
| | Extended Range Transmitter: | L × W × H 12" × 12" × 12" Weight 45 lbs |

Preferably, however, the users movement must be monitored and processed by the PC in real time. All major limb segments must be read. One known motion tracking system is called the Motion Star Wireless from Ascension Technologies. It is a wireless solution that can read up to 20 sensors in real time. This will allow the sensors to be positioned on the major limb segments (such as the upper arm, lower arm, hand, head, etc.) and be able to transmit the position and orientation of each of the segments to the PC with a high degree of accuracy. This kind of tracking is known as a 6DOF (Six Degrees of Freedom) tracker. In other words it will track 6 elements—The x, y & z positions and the azimuth, elevation and roll of each of the sensors.

All measurements are taken relative to what is called a source (or transmitter). This is a separate unit which sits some way from the user (but within a defined range) and it emits magnetic fields, which the sensors on the user will cut through. Cutting through these fields creates an interference at that point, which can be detected by the tracking unit.

This allows the major movements of the human to be monitored by the system and the information to be processed and applied to the users avatar (representatives of himself/herself).

However, smaller limb segments, such as the fingers, need to be processed so that the system knows when the user makes specific hand gestures. For this to work, we require the use of data gloves for both hands. These gloves can read the positions of the various fingers and provide the PC with the required information, and it can be used effectively with the motion tracking system explained above.

The user must also be able to sense when he is touching something. Whatever he touches must feel like the real thing. For instance, he can touch a smooth or rough surface. Each of these surfaces must feel different.

An approach to this tactile problem is to use the Cybertouch data glove for both hands. This data glove has 18 sensors and can measure the movements of the hand quite accurately. It also features small vibrotactile stimulators on each finger. Each one of these stimulators can be programmed individually to vary the touch sensation, so that when the users hand it 'touching' an object in the virtual world, a pre-programmed actuation profile can be set in motion so that the stimulators would simulate the effect the object has on the users fingers. The glove can also be programmed in such a way so that the user feels that he is touching a solid object.

Being able to program the touch sensations in this way is important, especially if the user wishes to feel the virtual skin of the other person.

The Doll

In the case of a female doll it is preferred to provide motion tracking, movement sensing, temperature sensing and pressure sensing. In the interests of economical production, motion tracking of the doll is envisaged to be limited to critical joints such as hip, knee, elbow, shoulder and head as well as the pelvis. Movement sensing could however be limited to the mouth, nipple area and vaginal area with temperature sensing in the vaginal area and pressure sensing at the nipple areas.

Figure 2:
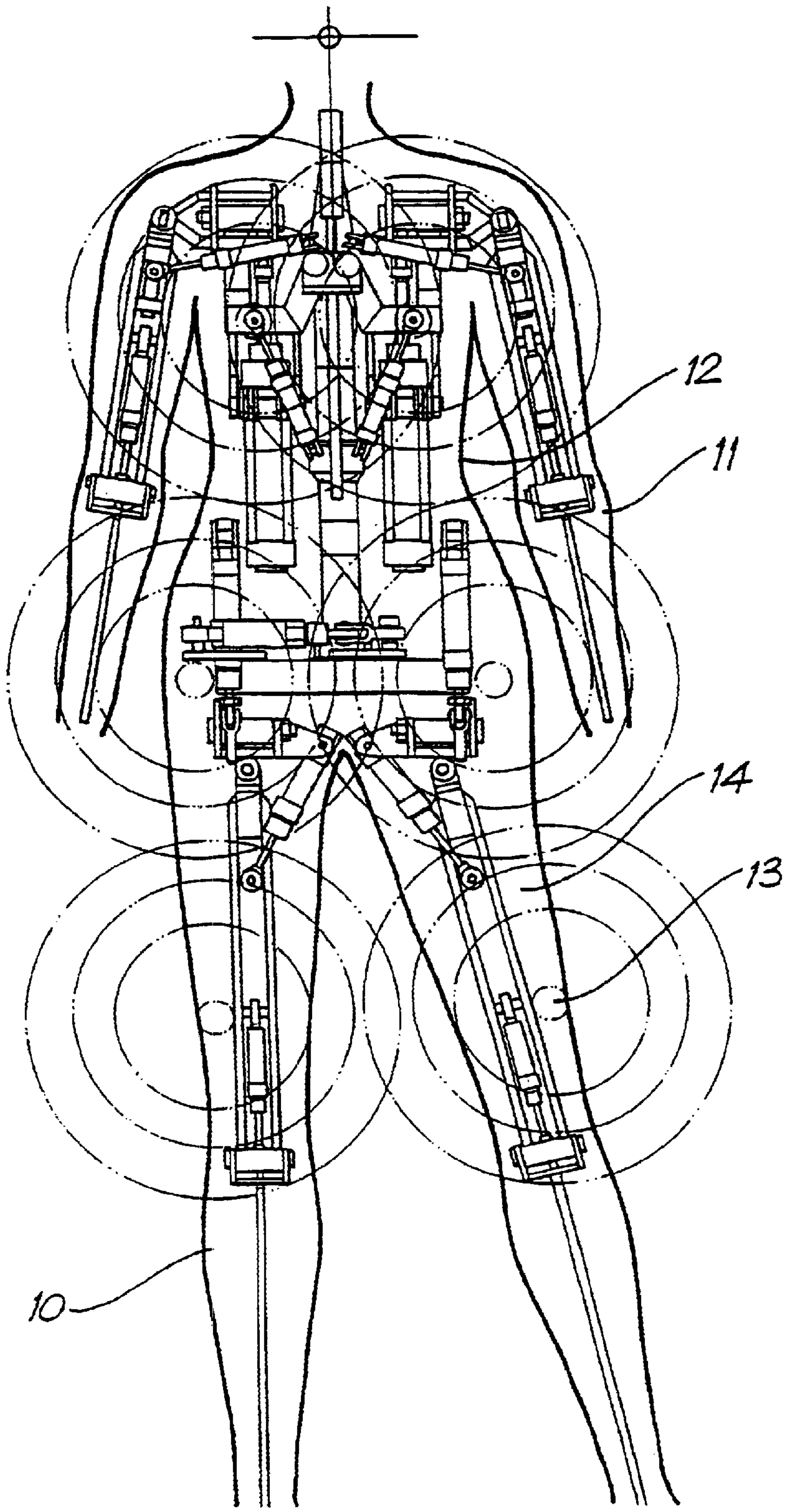
FIG. 2 is a schematic drawing of a doll embodiment.

Referring to FIG. 2 is a schematic drawing of a doll which with appropriate genitals added can function as either a male or female doll. The doll is intended to be of life-size form and have legs 10, arms 11, a head (not shown) and a torso 12. The outer structure would be of a flexible plastic material and incorporated within the doll but not shown is preferably a system for warming the temperature to normal skin temperature so that the doll closely mimics the touch of a human body.

Within the body is mounted an array of hydraulic actuators connected to a hydraulic system which is logic controlled so that a computer driven signal can cause responsive motion in the doll.

Also the doll incorporates pressure sensitive zones having each a focus 13 and a less sensitive peripheral region 14 so that touch applied can be used as a computer control signal whereby corresponding or even random actuation of actuators in the doll can cause movement.

In a preferred embodiment the doll has its portion defining the cavities used for sexual gratification to be removable for cleaning purposes.

The above described embodiment is for a female doll but a similar application can be to a male doll.

Figure 3:
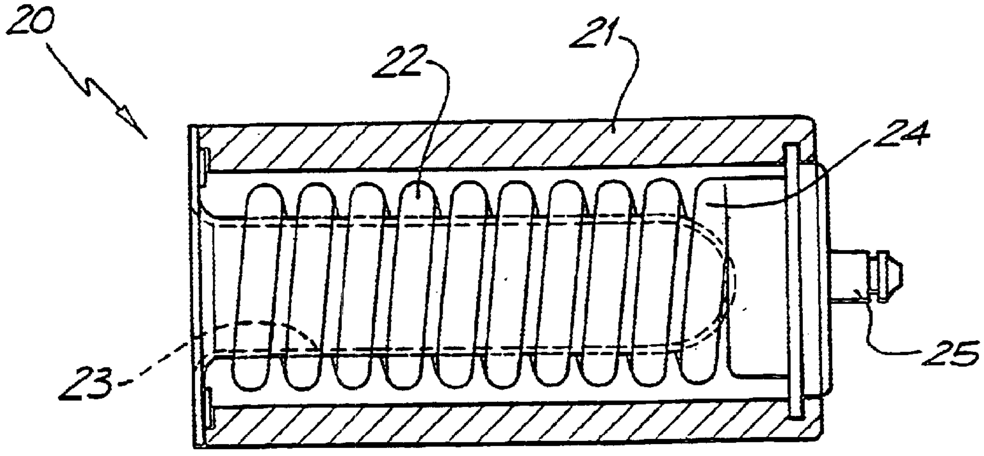
FIG. 3 is a schematic illustration of a female cavity embodiment.

Referring now to FIG. 3 there is a schematic illustration of an artificial vagina for fitting into a corresponding cavity in the doll. The artificial vagina has an outer cylindrical casing 21 within which is mounted a spiral inflatable tube 22 which surrounds an inner wall schematically shown in doted lines 23. A soft flexible plastic material is used. The inward end portion 24 of the spiral tube is connected through a quick-fit connector 25 to a supply of pressure fluid such as compressed air. On actuation of the system pressure fluid is supplied to the spiral tube which can thereby move and if desired the software controlling pressure fluid could cause rippling or vibration along the device. The quick-fit connector 25 permits the entire unit readily to be removed for cleaning purposes.

Figure 4:
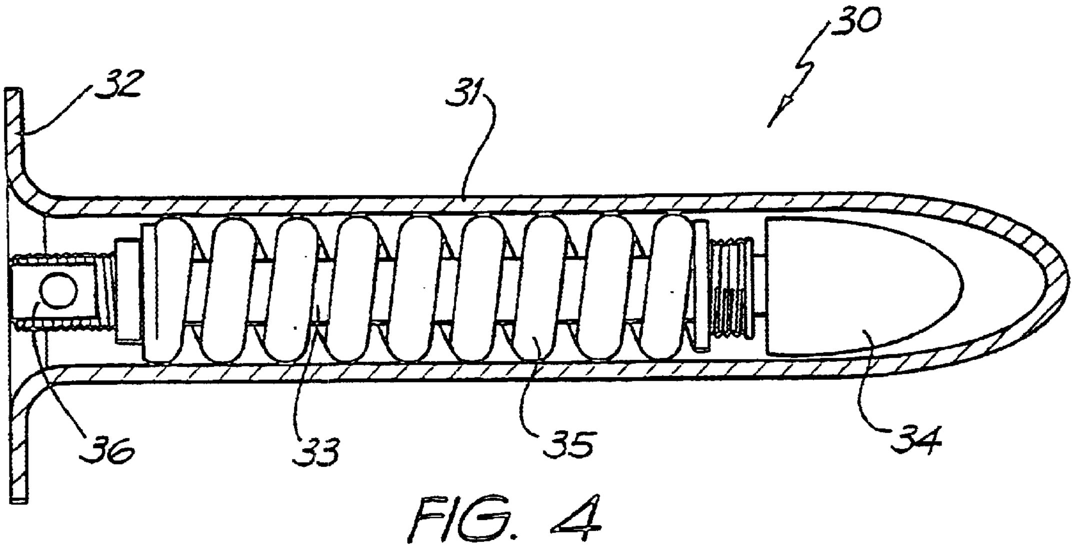
FIG. 4 is a schematic illustration of a male fitting embodiment.

Referring now to FIG. 4 an artificial penis for fitting to the doll is shown. The penis 30 has an outer sheath 31 of soft flexible plastic material and adapted to be warmed if desired to a normal body temperature. The sheath terminates in a mounting flange 32 which facilitates connection to the doll e.g. through hook-and-pile connectors (not shown). Within the penis is a pressure fluid actuator 33 which has a displaceable soft plastic tip portion 34 so that in use actuation causes longitudinal extension. The penis also incorporates a spiral inflatable tube 35 adapted to be connected to a pressure fluid so that with appropriate control radial expansion can now be achieved and if desired pulsation or other effects can be provided. A quick-fit connector 36 is provided for mounting the entire penis on the body in a physically supported form and connecting both the spiral tube 35 and the actuator 33 to a controlled system of pressure fluid.

The doll will be interfaced with the PC via either the existing ports.(parallel, serial, etc). However, this all depends on the complexity of the data that is being fed into the PC.

Another approach would be to use an interface card (such as an Analogue to digital converter card) to receive and output signals.

The software runs a separate process to monitor this card. Any data received from any of the ports would be processed and acted upon. Each limb segment of the doll is preferably controllable. In such a case a signal is sent to the doll to move the appropriate part.

The doll will be responsible for providing any information (i.e. where it's been touched, etc). This information is transmitted to the PC via an interface card and the software would act appropriately, i.e.. it could select from a list of appropriate limb movements. Once chosen, it would output the data to the 'doll controller' which would move the selected limbs accordingly.

Computer System

A typical personal computer system suitable for driving the system would be one having a Pentium III processor with RAM of 500 Mb 10 ns or faster, a large hard disc and a three-dimensional graphics card. Windows NT would be a suitable operating system. A typical specification is:

The system will be PC based and be the highest spec possible at the time. Currently a high specification PC would comprise:

Dual Pentium III 850
512 MB–1 GB RAM
Geforce 256 32 MB 3D AGP accelerator card
20 GB hard disk
Windows 2000
100 Base-T network card
Motion Star Wireless Tracking System (suggested)—Technical Spec attached
2 CyberTouch Gloves (suggested)—Technical Spec attached
Kaiser XL50 Headset (suggested)—Technical Spec Attached A two-user system will comprise another PC of the same specification that can be linked up via the network cards.

Software

To develop the database on which the software operates, an object scanner is used to collect three-dimensional images of head and body. The three-dimensional scanned image can then be meshed onto a database of a standard human movement which is with reference to standard points of movement which can be toes, ankles, knees, hips, pelvis, shoulders, elbows, wrist, neck and head.

Software is used to approximate where all the significant facial muscles are on the meshed frame and maps this on the individuals rendered face so that a software graphics engine can be used to render the mesh thereby generating the character so that the desired visual expressions can be created.

To provide a database of images photographic or video recording is made of a variety of scenes (sex or otherwise) each with a blue background so that this can be superimposed on selected backgrounds such as landscapes. Frame by Frame processing is then conducted to create library of sex positions.

To provide suitable audio output a recording is made of phrases and words which are stored in 16-bit quality on a database and the reproduction of such phrases and words will be linked to corresponding movement of the characters mouth muscles.

FIG. 1 is a dataflow diagram illustrating signal processing from inputs from a headset, a pelvis tracker, a data glove and a doll with outputs to the headset and to the doll and, as indicated, control of the doll can include activation of the limbs or body components, activation of lubricant dispensing and activation of heat.

Preferably implementation of signalling is through a wireless system such as the Motion Star Wireless System, the key advantages of which are set out below:

MotionStar Wireless utilises pulsed DC magnetic fields emitted by its extended range transmitter to track the position and orientation of its sensors. Sensors are mounted at key body points on your performer. Inputs from the sensors travel via cables to a miniature, battery-powered electronics unit mounted in a "fanny" pack. From here, sensor data and other signals from body-mounted peripherals, such as data gloves are sent through the air to the base station. They are then transmitted to your host computer via RS-232 or an Ethernet interface.

Application

Character Animation for TV, Movies & 3D Games

Live Performance Animation

Sports & Medical Analysis

Biomechanical Analysis

Human Performance Assessment

Interactive Game Playing

Rehabilitative Medicine

Key Benefits

Freedom of movement. No cables tether performer to a base computer.

Lightweight backpack for fast set-up, comfort and ease of use.

Large working area without elaborate installation procedures.

Highly portable motion-capture solution transports easily without calibration procedures.

Real-time motion capture eliminate post processing.

Instant interaction is allowable.

All-attitude tracking means data is never lost so a clear line of sight to the transmitter is not required.

Tracks multiple characters simultaneously.

Cost effective motion-capture solution recoups your investment in one project.

In summary the avatar should be designed having regard to the following description.

In both the single user and the user-user scenarios, the actions and reactions of the avatars will be based on a set of inputs received from the user(s). The various limb-tracking devices will allow the software to know exactly what each user is doing, and with the additional devices and sensors on the body, the software is aware of information regarding a range of other states. When applied to their representing avatar, these alterations will add to the accurate portrayal of their level or state of arousal. These would include; User temperature, resulting in altering his/her avatar flesh tone. User breathing, resulting in exaggerated/deeper chest movements, and be additional to the information being passed by any hardware devices associated with the users genitalia.

In the single user environment, motion capture is still currently the best method for attaching life-like attributes to a computer-generated person. For example; a persons posture, mannerisms, and gestures are all carried through to the character when using motion capture data—these are the qualities that will make the animations look real, even without the presence of another actual person. The software would continuously monitor the users actions, and adapt the computer-controlled avatars reactions accordingly.

In the user-user environment, all of the limb movements of the avatars will be controlled directly by the users by means of their tracking devices. Facial expressions could be registered in several ways, the simplest being a choice of buttons, but the most effective being the use of additional sensors monitoring the users face movements .(or LIPSinc described earlier). These would be translated into the morphing animations and animated textures on the appropriate avatar, as detailed previously.

In designing a preferred form of system for the present invention, realistic tactile experiences are desired and the preferred system is designed in accordance with the following:

All objects, including humans, would have a weight attribute associated with it. In the case of the human, each of his/her limbs would have a weight value. The speed of push from the other person can be read by measuring the time it takes for the limb segment to move from one position to the next. From this, and the mass/weight of the users virtual arm, we can determine the force applied at the collision point. Then, depending on the weight being pushed, we can move the object/human accordingly. In the case of the human, a set of animations would be set in motion to make the appropriate move. i.e. if the force was enough to push the person back, he would step back. A stronger push could be enough to make the other person fall, depending on where the force was applied. In this case an appropriate 'fall' animation would be applied.

If the hand met the other persons skin, the skin would push in slightly according to its elasticity and hardness factors. Of course, there will be a limit here to make things realistic. When this 'stretch' limit is reached, this is when the person would be subjected to a 'movement' type force. i.e. the force is strong enough to push the player somewhat, rather than merely effecting the skin.

You can go a step further and have an extremely complex physical system simulated. In this case, each limb segment has a weight which depending on where it is positioned would make the person move according to any outside forces such as gravity. For instance, to get the person to stand, one would have to position the legs and body in such a manner that the body's centre of gravity would keep him standing. If one of the legs were to be lifted off the floor, the person could fall if the weight distribution was such that this would occur. Each limbs segment would have min./max. limits, so that they could only be positioned according to human limits.

Added to this, a 'self preservation' A.I. engine could be built in which would react to any outside force.

In other words, if another user were to push this 'virtual' person, it's A.I. engine would force the limbs to react in such a way to prevent itself from falling.

This would separate it from other inanimate objects, which would just get pushed or fall.

Gravity, friction, etc can all me modelled into the virtual space, providing a very realistic version of the real world. However, it will always be a simpler version due to the limitations of the software/hardware. A two-user networked experience can be achieved with embodiments of the invention.

Rather than having a virtual human with associated artificial intelligence, this system would have the virtual human replaced by another user. His or her movements (tracked by the tracking hardware) would be applied to the polygon mesh representing them within the virtual world. Their representation within the world is known as an avatar (described in more detail later). The user can choose this avatar before entering the environment. It could be a famous personality for instance. The other user would see this user as that personality.

What this system would require, however, would be a PC system per user linked up via a local area network. The network bandwidth would have to be sufficient to allow the PC's to transmit the user movements to the other PC in real time with very little or no lag. Information such as the users position and orientation in the world, along with all the positions of the limbs and fingers, etc would have to be transferred to the other user, so that he/she can see them within the same shared environment. The users must also be allowed to verbally communicate with one another. This can be achieved by linking the audio cards on both systems to allow for this as the users may be in separate rooms.

For the purpose of virtual reality applications, the software to be created will allow the user to enter a virtual world and have a sexual experience with either a virtual human, or another actual human, portrayed within the software by an avatar.

The use of computer generated imagery in virtual reality means that both the avatars, and the environments they are to be experienced within, can be many and varied.

Taking a film star scenario as an example, the activity could take place anywhere from a penthouse apartment to a luxury yacht. It is therefore possible to generate extensive libraries of both avatars and venues for the user to select from.

The work involved in the origination and eventual processing of these options (avatar and environment) is quite different, and the factors and options that are involved in this development are outlined below.

In order to understand the graphics methods we are able to exploit within the software applications we develop, it seems sensible for us to firstly explain the basic principles of 3D. Creating Objects for use within a Virtual World.

Sound handling is a desirable component of the preferred embodiment since sound is obviously an important part of the overall experience. Sound must be sampled at a high enough bit-rate and frequency to make it realistic.

Provision for positional audio must also be made. In other words a sound of a car in the virtual world must appear to originate from the car. This is known as 3D sound localisation, and software development kits are available to provide the programmer with the necessary algorithms to program such sounds.

The sound can be positioned within the virtual world in a similar way to positioning a polygon mesh object.

However, the sounds would also have a number of other attributes, such as:

Minimum and maximum range. The sound at a particular point would change volume according to where the user is in relation to these specified ranges.

Sound cone. This is made up of an inside cone and an outside cone. Within the inside cone, the volume of the sound would be at a defined level (also dependant on the range from the sound source). Outside the outside cone, this volume would be attenuated by a specified number of decibels, as set by the application. The angle between the inside and the outside cones is a zone of transition from the inside volume to the outside volume.

Velocity. This attribute would be used for creating Doppler shift in the sound.

Applying these kind of sound properties can add dramatic effects to the experience. For example, you could position a sound source in the centre of a room, setting its orientation toward an open door in a hallway. Then set the angle of the inside cone so that it extends to the width of the doorway, make the outside cone a bit wider, and set the outside cone volume to inaudible. A user moving along the hallway will begin to hear the sound when near the doorway, and the sound will be loudest as the listener passes in front of the open door.

These sounds can also be positioned at the mouth of the virtual human for speech. The speech sound samples would be linked to a set of mouth and facial animations, thus it would appear that this virtual human is speaking. The possibilities are endless.

The tracking hardware has limitations. They can only work accurately within a certain range of the source. Depending on the tracking solution employed, this range can be around 3 to 4 metres. However, it is not realistic to allow the user to only move this amount within the virtual world, so another method of navigation is required. The problem can be illustrated thus:

The virtual world is a large apartment. The user is required to walk from the doorway to the kitchen, which is located 10 metres away. In the real world the user can only move 3–4 meters before the tracking system stop working accurately.

A number of methods can be employed here. One of which is to incorporate a game pad. So if the user presses the forward button, he moves forward in the virtual world, etc. This however, is a little cumbersome, as you would want the user to have both hands free to interact within the environment freely. Another solution would be to employ a treadmill type device, so that the user can physically walk. The treadmill would move under his feet and the PC can measure the amount of movement, and move the person within the virtual world accordingly.

Yet another solution is to allow the user to walk on the spot. The sensors attached to his legs and feet can be monitored for 'walking type' movements and thus he can be moved accordingly within the virtual environment. All these solutions need to be explored to determine which is the most realistic.

There will be certain areas of the world that the user cannot move. For instance, there may be obstacles, like beds, chairs, etc. The user must be forced to stop moving if any of these kind of items are in the way. This programming task is called collision detection. Simply put, the users current and last positions are taken. This produces a 3D line that can be used to check if it intersects any of the objects within the world. If so, a collision is flagged and the user is forced to stop. A more complex collision algorithm can be incorporated which takes into account the positions of the users feet (measured with the tracking sensors). This more complex solution would determine if one of the users feet were over the object. Thus allowing him to either step onto or over the object.

As well as navigating within the environment, the user must be allowed to interact with various virtual objects. For instance he may wish to pick up a glass of wine. This programming problem can be broken down into a number of stages:

Detect the 3D world position of the users hands.

If the hand is within a specified range of the object, perform the following tests:

Can the object be picked up?

If so, check the positions of the fingers on the hand and attempt to recognise a gesture which indicates the object requires picking up.

If the appropriate gesture is made, attach the object to the hand as long as the gesture remains similar.

If the hand gesture changes, drop the object until it hits a surface in the world.

If the object is not within range, check any other objects.

Basically, the users hand position within the virtual world can be tracked using the motion tracking hardware mentioned previously. This position is then continually monitored against certain types of objects that are previously flagged as 'pickup-able'. For instance, a bed would not be flagged as such as this would not be in the context of the experience, however, a glass of wine would be. Each of these flagged objects would have certain attributes programmed:

Pick Up Range. If the users hand is within this specified range, this object can be picked up as long as the users hand is making a certain gesture (i.e. a fist).

Weight. This can be used to activate the stimulators in the data glove to make the user feel the object being picked up.

Smoothness/Hardness Factors. These can also be used to activate the finger stimulators to allow the user to feel the surface of the object.

The hand position would be compared to that of any of these flagged objects. If the range between the hand and the object is within the specified range, a more complex algorithm is used to determine the positions of the fingers relative to the object. There are two possible method that can be employed here, depending on the complexity of the experience required.

Simple Gesture Recognition. As the software can read the positions of the fingers (read in from the data glove) simple checks can be made to determine if the user is making a point, fist or open hand gestures. So if the hand is within range of an object and the user makes a fist gesture. The software would detect this and attach the object to the hand. Wherever the hand moves now, the object would move with it. In effect, the user has picked up the virtual object. If he now makes an open hand gesture, the software would detect this and drop the object from the hand. This system is very basic and not realistic, as in real life people do not make fists for everything they pick up!

Finger Collision Detection. This is a more complex algorithm that reads the positions of the fingers and palm and determines which parts of the object they intersect with (or touch). If two or more fingers touch the object and the fingers are positioned such that they lie on opposite sides of the object (or indeed under the object) then it can be picked up. As such it will then attach itself to the hand. A system such as this requires further investigation to determine the best way to incorporate the algorithm.

All objects within the world (whether pick up-able or not) must have attributes pre-assigned to them, such as smoothness, elasticity, hardness, etc. So if the user touches any of these objects, depending on the hardness and elasticity, the object would deform a certain amount and spring back once it is let go. This can be achieved by performing collision detection with the various parts of the users hand. As we can monitor the position and orientation of the hand, and subsequently the fingers, we already are aware of the position within the virtual world. As such we can detect, for instance, if the fingers touch the surface of the virtual humans skin. This skin would have these attributes set and would deform a certain amount obviously, this deformation must stop at some point to make it realistic, and thus the sensation in the stimulators would increase indicating that a threshold has been reached. The virtual hand represented would also be prevented from going any further.

The smoothness factor could be used to create certain sensations to the users fingers via the stimulators, so that the user can feel how rough a surface is.

Interaction with A Virtual Actor

As the virtual human (and any other object within the world for that matter) is made out of a polygon mesh (a collection of triangles), these meshes must be detailed enough to allow a small area of the object to be deformed. Deformation occurs by moving the effected polygons, in the area of the collision with the finger, away from the finger. If the polygon detail were low, this would mean a larger area would be affected, which is not realistic. However, the frame rate is a major issue. This is defined as the time it takes to render one frame of the scene. If there were a high polygon count in any one scene the frame rate would reduce due to the extra overhead of processing the visible polygons. To counter this, we would utilise what's called level-of-detail processing (LOD). Basically, this is a process by which we reduce the number of polygons that are being rendered on an object the further away it gets from the user.

For instance, when a car is near the user it needs to be quite detailed. The user must be able to see components of the car such as the steering wheel,.etc. However, you would not want to see as much detail if the car was says 20 metres away. Thus a simple algorithm would be to have 2 versions of the same car. One with the steering wheel and a high polygon count showing the curvature of the body and another that has a lower polygon count and no internal details (like the steering wheel). The algorithm would then switch between the high resolution model and the lower one depending on how far the user is from it, thus the computational overhead is reduced as the overall scene becomes less complex the further the objects are away from the user. Obviously, this is a very simple example that only has 2 levels of detail (i.e. the 2 models). The eventual application can have multiple levels of details depending on the usage. In the example above if the car was half a mile away, you would only want to render a very basic model, as there is no point in rendering detail inside the car.

Basically, in this project you would have a simpler model of the virtual human if they were some distance away and switch to a higher polygon count one as they come closer. The artists would engineer the transition between a lower to higher resolution model to be unnoticeable.

As the user would be quite close to the virtual human when he touches her, the model would be of sufficient resolution to make the skin look realistic in it's movement.

Virtual Actor Animation

All objects within the environment are made from polygon meshes. The virtual actor is no different. Each polygon is effectively a 2D triangle positioned in 3D space, and each corner of the triangle (the vertex) has an x, y, z coordinate that specifies where in the world that point is.

Animating such an object involves moving each of these triangles in such a way to make the whole thing look realistic. To make a virtual human walk, for instance, would involve creating a number of frames of animation in which each frame has the polygon mesh in a different position. The virtual human would then have to move through each of these positions by interpolating the points in between to make a smooth animating human.

To pre-input this data by hand is time consuming and is limited to the artists ability to create a realistic motion. However, to make life a little easier, motion capture can be utilised. This involves having an actor wear a number of sensors around his body and record all the sensors positions and orientation as he moves into a data (or animation) file. This file can then be read later by the eventual application and provide the necessary frame data for the virtual human to follow. Thus a very realistic movement can be achieved.

Motion capture can also be employed to provide information on mouth movements and facial movements, so that facial animation can be utilised. Thus the virtual human can be made to act extremely realistically.

What is claimed is:

1. An apparatus for providing a virtual reality sexual experience, the apparatus comprising audio reproduction means, visual reproduction means, tactile means for sexual stimulation of a user and being in the form of at least a part of a mannequin, a control system to correlate the audio reproduction means, the visual reproduction means and the tactile means to relate to one another to simulate a sexual experience, a computer based drive system to provide a scenario for audio and visual outputs which is selected from a database and which allows for visual and audio outputs in a manner corresponding to user movements and engagement with the tactile means, movement and position sensing means responsive to a part of the body of the user and adapted to provide a control input to the computer based drive system, and wherein the part of the mannequin has sensors which provide control signals to the control system to alter the audio and the visual outputs corresponding to physical interaction of the user with the part of the mannequin.

2. The apparatus of claim 1 further having means to produce physical reactions on the part of the mannequin in a manner which represents a simulated sexual reaction.

3. The apparatus of claim 1 wherein the part of the mannequin comprises a genital unit having a cylindrical body portion and a flexible tube adapted to be connected to a source of pressure fluid and to a control system whereby the flexible tube in response to software commands can execute movement.

4. The apparatus of claim 3 wherein the flexible tube is cylindrical and the control system regulates for the pressure fluid whereby expansion and contraction of the flexible tube is achieved.

5. The apparatus of claim 2 wherein the simulated sexual reaction is selected from at least one element selected from the group consisting of heat, suction, pressure, vibration, lubrication and ejaculation.

6. The apparatus of claim 1 wherein the database includes images of a set of potential virtual sexual partners, and the computer based drive system causes the images to progress in a manner correlated with the user's position and movement.

7. The apparatus of claim 1 wherein an entire mannequin is included with moveable and responsive body parts.

8. The apparatus of claim 1 which includes a head mounted display system for the user for virtual reality creation.

9. The apparatus of claim 1 which includes a digital glove-like device to be fitted to the hand region of the user for providing the movement and the position sensing means.

10. A user interactive apparatus for providing a virtual reality sexual experience, the apparatus comprising:

audio reproduction means having an audio output;

visual reproduction means having a visual output;

tactile means for sexual stimulation of a user and including at least a part of a mannequin, the part of the mannequin being associatable with the user, and the part of the mannequin having movement sensing means and position sensing means responsive to movement and position of the body of the so associated user;

a control system for correlating and interrelating the audio reproduction means, the visual reproduction means and the tactile means relative to one another;

the control system including a data base and a computer-based drive system for providing a scenario output for the audio output and the visual output;

the part of the mannequin further having control signal generators that are responsive to the movement sensing means and the position sensing means and that provide signal outputs that are received by the control system and that are responsive to, representative of, and correlated with body movements of the user when the user is so associated with the tactile means;

the control system further including software that is responsive to the database and to the received signal outputs, and that regulates the scenario content so that the audio output and the visual output are correlated with and correspond to movements of the user;

thereby to simulate a sexual experience for the user.

11. The apparatus of claim 10 wherein the data base includes more than one scenario output type and wherein one scenario output type is selectable by the user.

12. The apparatus of claim 10 which further includes a head mounted display system for the user that provides audio output and visual output of the scenario.

13. The apparatus of claim 10 wherein the user is associated with a user body motion tracking device, and the device provides signal outputs that are output to and used by the control system in determining the scenario content.

14. The apparatus of claim 10 wherein a glove-like device is fitted to at least one hand of the user for tracking of hand motion and for providing output signals that are output to and used by the control system in determining the scenario content.

15. The apparatus of claim 10 wherein the mannequin comprises an entire body with moveable component parts.

16. The apparatus of claim 10 which is linked to more than one user.

* * * * *

UNITED STATES PATENT AND TRADEMARK OFFICE

CERTIFICATE OF CORRECTION

PATENT NO. : 6,695,770 B1
DATED : February 24, 2004
INVENTOR(S) : Choy et al.

It is certified that error appears in the above-identified patent and that said Letters Patent is hereby corrected as shown below:

Title page,
Item [75], Inventors, change "Davies" to -- Daevys --.

Column 7,
Line 36, after "artificial vagina" insert -- 20 --.

Column 10,
Line 3, delete the period after "movements"

Column 13,
Line 60, after "amount" insert a period.
Line 60, change "obviously" to -- Obviously --.

Column 14,
Line 20, delete the period after "wheel,"

Signed and Sealed this

Twenty-seventh Day of July, 2004

JON W. DUDAS
*Acting Director of the United States Patent and Trademark Office*